(12) United States Patent
Do et al.

(10) Patent No.: US 8,591,871 B2
(45) Date of Patent: Nov. 26, 2013

(54) USE OF GLUTAMIDE STABILIZERS

(75) Inventors: Thi N. Do, West Orange, NJ (US);
Freda E. Robinson, Nyack, NY (US);
Robert E. Kalafsky, Ogdensburg, NJ (US)

(73) Assignee: Avon Products, Inc., New York, NY (US)

( * ) Notice: Subject to any disclaimer, the term of this patent is extended or adjusted under 35 U.S.C. 154(b) by 169 days.

(21) Appl. No.: 12/979,539

(22) Filed: Dec. 28, 2010

(65) Prior Publication Data
US 2012/0164093 A1  Jun. 28, 2012

(51) Int. Cl.
*A61Q 5/00* (2006.01)

(52) U.S. Cl.
USPC .................................................. 424/70.12

(58) Field of Classification Search
None
See application file for complete search history.

(56) References Cited

U.S. PATENT DOCUMENTS

| | | |
|---|---|---|
| 3,969,087 A | 7/1976 | Saito et al. |
| 5,362,482 A * | 11/1994 | Yoneyama et al. ............ 424/69 |
| 6,210,690 B1 | 4/2001 | Nabeshima et al. |
| 6,214,329 B1 * | 4/2001 | Brieva et al. .................. 424/70.7 |
| 6,451,294 B1 | 9/2002 | Simon |
| 7,138,128 B2 * | 11/2006 | Bleckmann et al. .......... 424/401 |
| 7,175,835 B1 * | 2/2007 | Simoulidis et al. ............. 424/59 |
| 7,244,419 B2 | 7/2007 | Yamato et al. |
| 7,276,547 B2 | 10/2007 | Pinzon et al. |
| 7,314,612 B2 | 1/2008 | Ferrari et al. |
| 7,342,992 B2 | 3/2008 | Schomberg |
| 7,351,418 B2 | 4/2008 | Collin |
| 2003/0026821 A1 | 2/2003 | Rando et al. |
| 2005/0118122 A1 | 6/2005 | Simon et al. |
| 2006/0078581 A1 | 4/2006 | Yamato |
| 2009/0280077 A1 | 11/2009 | Yoshida et al. |
| 2010/0166684 A1 | 7/2010 | Kokeguchi |

\* cited by examiner

*Primary Examiner* — Jyothsna Venkat
(74) *Attorney, Agent, or Firm* — David M. Joyal; Joan M. McGillycuddy; Brian C Remy

(57) ABSTRACT

Fluids are provided which resist phase separation by inclusion of a stabilizing amount of a glutamic acid derivative in the presence of ethanol. The fluids comprise an aqueous discontinuous phase, a silicone oil containing continuous phase, a glutamic acid derivative such as dibutyl ethylhexanoyl glutamide, and ethanol. The fluids may be prepared without heating to solubilize the glutamic acid derivative.

1 Claim, No Drawings

USE OF GLUTAMIDE STABILIZERS

FIELD OF INVENTION

The present invention relates to methods for stabilizing emulsions and other fluids having more than one phase. More specifically, the invention relates to the use of glutamic acid derivatives to stabilize such compositions.

BACKGROUND OF THE INVENTION

Emulsions are well-known in the cosmetic and personal care fields due to their desirable aesthetics. A water-in-silicone oil emulsion has a discontinuous aqueous phase and a silicone-containing continuous phase. However, these emulsions have only limited stability and will separate into two phases over time unless an emulsifier or other emulsion stabilizer is used.

Examples of water-in-silicone emulsifiers include dimethicone polymers having pendant polyalkylene oxide chains, such as dimethicone copolyols. These emulsifiers may be included at levels up to 10% by weight to achieve stable water-in silicone emulsion. However, in some instances, the properties of a product or its intended functionality may require that the amounts of these emulsifier be reduced or altogether eliminated. It is therefore an object of the invention to provide stabilized water-in-silicone emulsions that do not rely on high levels of dimethicone copolyols for stability.

SUMMARY OF THE INVENTION

In accordance with the foregoing objectives and others, the present invention provides emulsions and other multi-phase fluids stabilized with a glutamic acid derivative such as dibutyl ethylhexanoyl glutamide.

In one aspect, the invention provides stabilized emulsions, which may be, for example water-in-oil, oil-in-water, silicone-in-water, or water-in-silicone emulsions, containing from about 0.02% to about 0.8% by weight dibutyl ethylhexanoyl glutamide.

In another aspect of the invention, a method is provided for stabilizing a fluid having an oil phase and a particulate phase homogenously dispersed throughout the oil phase, the method comprising incorporating in said fluid an amount of dibutyl ethylhexanoyl glutamide effective to inhibit separation of the particulate phase from the oil phase. The particulate phase may include, for example, hydrophobically modified alumina and/or silica particles.

In a related aspect, a method is provided for stabilizing an emulsion having an oil phase, a water phase, and a particulate phase, the method comprising incorporating an amount of dibutyl ethylhexanoyl glutamide effective to inhibit separation of the particulate phase from the emulsion. The particulate phase may include, for example, hydrophobically modified alumina and/or silica particles.

In a related aspect, a stabilized emulsion is provided comprising (i) an oil phase having, as the major component, a silicone oil, (ii) an aqueous phase comprising water, and (iii) an amount of a glutamide compound, typically dibutyl ethylhexanoyl glutamide, sufficient to stabilize the emulsion and thicken the non-aqueous phase such that the phases do not separate for at least two weeks at 25° C. In one variant the oil phase constitutes a continuous phase of the emulsion and the aqueous phase constitutes a discontinuous phase.

The glutamide compounds of the invention typically have the structure according to formula (I):

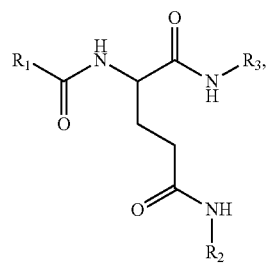

wherein, $R_1$, $R_2$ and $R_3$ are each independently selected from branched, straight chain, or cyclic alkyl groups having from three to 20 carbon atoms, and preferably $R_1$ is selected from branched, straight chain alkyl groups having from five to 16 carbon atoms, and $R_2$ and $R_3$ are independently straight chain alkyl groups having from three to six carbon atoms, and preferably, $R_1$ is selected from branched or straight chain alkyl groups having from five to 16 carbon atoms, and $R_2$ and $R_3$ are each n-butyl groups. In one implementation, $R_1$ is a straight chain undecyl group and the compound of formula (I) is Dibutyl Lauroyl Glutamide. In another implementation, $R_1$ is a 1-ethylpentyl group the compound of formula (I) is Dibutyl Ethylhexanoyl Glutamide, having the structure of formula (II):

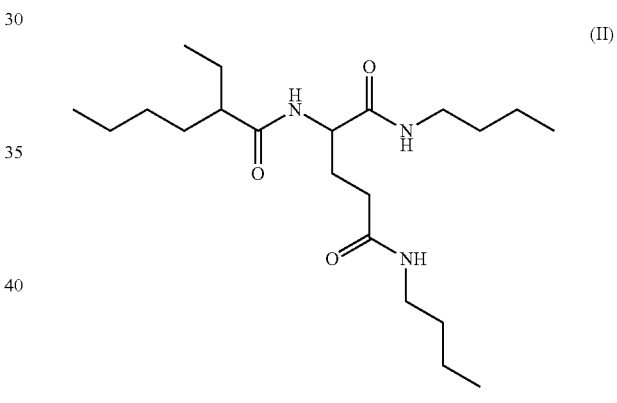

The glutamide compounds according to formula (I) or formula (II) will typically be present in an amount of from about 0.005% to about 4.0% by weight of the emulsion, but will more typically be present in an amount of from about 0.02% to about 0.8% by weight, from about 0.02% to about 0.5% by weight, or from about 0.025% to about 0.1% by weight, or from about 0.03% to about 0.06% by weight of the emulsion.

The emulsions and multi-phase fluids are preferably stable for at least two weeks at room temperature (e.g., about 25° C.) but are also ideally stable over the same period at elevated temperatures of at 110° F., and cooler temperatures of 40° F. In some embodiments, the emulsions and fluids will be stable for at least two weeks at both 40° F. and 110° F. In the case of a multiphase fluid having a continuous oil phase and a particulate phase dispersed throughout the oil phase, stability may be measured by the resistance to sedimentation of the particulates.

The stabilized water-in-silicone oil emulsions will typically comprise a volatile silicone oil in an amount from about 20% to about 99% by weight of the emulsion and water in an amount from about 1% to about 70% by weight of the emulsion. More typically, the stabilized water-in-silicone oil emulsions will typically comprise a volatile silicone oil in an amount from about 20% to about 90% by weight of the emulsion and water in an amount from about 10% to about 50% by weight of the emulsion. The silicone oil will typically comprise a silicone fluid having a vapor pressure above about 0.01 mmHg at 20° C. and may be selected from the group comprising cyclomethicone tetramer, cyclomethicone pentamer, cyclomethicone hexamer, trisiloxane, methyl trimethicone, or combinations thereof, with cyclomethicone pentamer being preferred.

In preferred embodiments, the stabilized water-in-silicone oil emulsions will further comprise from about 1% to about 25% by weight ethanol. It has surprisingly been found that the addition of ethanol permits the glutamide stabilizer to dissolve in the emulsion at room temperature, without the need for pre-dissolving or melting it, and without the use of elevated temperatures which are incompatible with volatile silicone oils such as cyclomethicone pentamer. In a preferred embodiment, the emulsion will have cyclomethicone pentamer in an amount from about 30% to about 80% by weight of the emulsion, water in an amount from about 10% to about 45% by weight of the emulsion, and ethanol in an amount of from about 5% to about 15% by weight of the emulsion.

By using the glutamide stabilizers of formula (I) or formula (II), it is possible to eliminate or reduce the amount of emulsifier used. In one implementation the stabilized water-in-silicone emulsions will comprise a emulsifier in an amount of less than about 1% by weight of the emulsion. The preferred emulsifiers will comprise an organosiloxane polymer having side chains comprising $-(EO)_m-$ and/or $-(PO)_n-$groups, where the sum of n and m is about 50 or less, the side chains being terminated with hydrogen or $C_{1-8}$ alkyl groups, such as, for example, PEG 10-dimethicone.

The stabilized water-in-silicone oil emulsions may further comprise additional components, such as non-volatile oils, water-soluble film formers, hydrophobic film-formers, silicone-based film formers, emollients, humectants, conditioners, silicone resins, gellants, pigments, fillers, sunscreens, preservatives, fragrances, antifoaming agents and the like.

The emulsion may be formulated as skin care products, hair care products, color cosmetic products or the like. Where the emulsions are intended for application to the hair, particular mention may be made of water-soluble film formers, such as polyquaterniums like polyquaternium-37 (INCI); silicone-based hydrophobic film formers, such as silicone acrylate copolymer which may comprise a poly(alkyl)acrylate backbone and a dimethicone polymer grafted to an alkyl ester side chain. The hair products may be "leave-in" products that are intended to be applied to the hair and not immediately rinsed off.

In preferred implementations, the emulsions will include particulates such as hydrophobically surface-modified oxides. Examples of hydrophobically surface-modified oxides include those selected from the group consisting of aluminum oxide, silicon dioxide, titanium dioxide, zirconium dioxide, tin dioxide, zinc oxide, iron oxide and combinations thereof, that have been surface modified with caprylylsilane. Particular mention may be made of fumed silica which has been surface modified with caprylylsilane and/or fumed alumina which has been surface modified with caprylylsilane, either of which may comprises from about 0.1 to about 1% by weight of said emulsion.

Also provided is a method for forming a stabilized water-in-silicone oil emulsion. The emulsions will have a continuous phase, the major component of which is a volatile silicone oil, and a discontinuous phase comprising water. The method generally comprises incorporating in the emulsion the compound of formula (II), having the CTFA name dibutyl ethylhexanoyl glutamide, and an amount of ethanol sufficient to permit the dibutyl ethylhexanoyl glutamide to dissolve in the emulsion at a temperature less than 40° C., that is, without the need of heating the emulsion. In some implementation, the dibutyl ethylhexanoyl glutamide dissolves at a temperature between 20° C. and 30° C., for example, at about 25° C.

The silicone fluid typically comprises a silicone fluid having a vapor pressure above about 0.01 mmHg at 20° C. in an amount from about 30% to about 80% by weight of the emulsion, the water typically comprises from about 10% to about 45% by weight of the emulsion, the ethanol typically comprises from about 1% to about 25% by weight of the emulsion, and the dibutyl ethylhexanoyl glutamide typically comprises from 0.01% to about 3% by weight of the emulsion. The volatile silicone oil is typically one which cannot safely be heated to elevated temperatures, and may be selected from the group comprising cyclomethicone tetramer, cyclomethicone pentamer, cyclomethicone hexamer, trisiloxane, methyl trimethicone, or combinations thereof. In one embodiment, the volatile silicone oil comprises cyclomethicone pentamer and the dibutyl ethylhexanoyl glutamide comprises from 0.01% to about 0.08% by weight of the emulsion.

These and other aspects of the present invention will become apparent to those skilled in the art according to the present description, including the claims.

DETAILED DESCRIPTION

The present invention provides compositions and methods for stabilizing emulsions or multi-phase fluids used in cosmetic and personal care products. As used herein, a multi-phase fluid is any fluid comprising two or more phases, in which one phase is a continuous phase. Multi-phase fluids include, without limitation, combinations of a liquid continuous phase with one or more liquid and/or solid discontinuous phases. A specific example of a multi-phase fluid is a silicone oil having a particulate phase homogenously dispersed therein.

A stabilized water-in-silicone oil emulsion according to the invention comprises (i) a continuous phase comprising a topically acceptable silicone oil, and (ii) a discontinuous phase comprising water. By "topically" acceptable" is meant that the component is generally regarded as safe for application to a human integument. The emulsions also comprise an amount of stabilizers derived from the amino acid glutamic acid sufficient to prevent or retard separation of the phases.

The glutamide compounds of the invention will have the structure according to formula (I):

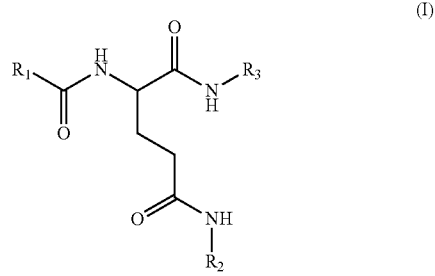

(I)

wherein, $R_1$, $R_2$ and $R_3$ are $C_1$-$C_{20}$ hydrocarbon moieties which may be straight chained, branched, or cyclic and which may comprise one or more heteroatoms selected from oxygen, nitrogen, and sulfur. $R_1$, $R_2$ and $R_3$ are independently selected at each occurrence and therefore may be the same or different. Preferably, at least one of $R_1$, $R_2$ and $R_3$ is a $C_5$-$C_{20}$ hydrocarbon moiety and more preferred still, $R_1$ is a $C_6$-$C_{20}$ hydrocarbon moiety.

Typically, each of $R_1$, $R_2$ and $R_3$ are independently selected from branched, straight chain, or cyclic alkyl groups having from three to 20 carbon atoms. $R_1$, $R_2$ and $R_3$ may, for example, each be independently selected from methyl, ethyl, propyl (e.g., n-propyl or isopropyl), butyl (e.g., n-butyl, isobutyl, tert-butyl), pentyl (e.g., n-pentyl, isopentyl, neopentyl, cyclopentyl), hexyl, heptyl, octyl, nonyl, decyl, undecyl, dodecyl, tridecyl, tetradecyl, pentadecyl, etc. In one embodiment, $R_1$ is selected from branched or straight chain alkyl groups having from five to 16 carbon atoms and $R_2$ and $R_3$ are independently straight chain alkyl groups having from three to six carbon atoms, namely propyl, butyl, pentyl, or hexyl. Preferably, $R_1$ is selected from branched or straight chain alkyl groups having from five to 16 carbon atoms, and $R_2$ and $R_3$ are each n-butyl groups.

In one embodiment, $R_1$ is a straight chain undecyl group and the compound of formula (I) is Dibutyl Lauroyl Glutamide. In another implementation, $R_1$ is a branched heptyl group, more specifically a 1-ethylpentyl group, and the compound of formula (I) is Dibutyl Ethylhexanoyl Glutamide, having the structure of formula (II):

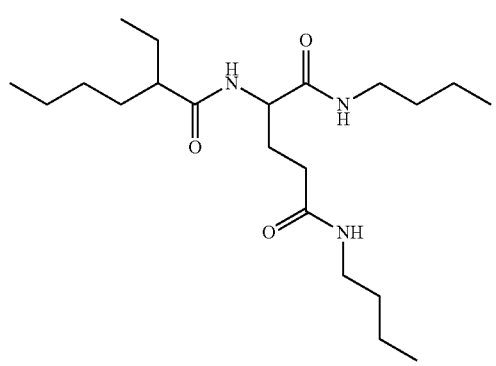

(II)

A glutamide compound "consisting essentially of" dibutyl ethylhexanoyl glutamide is intended to mean that the presence of additional glutamide compounds in amounts which would measurably affect the stability and/or viscosity of the fluid are excluded.

The glutamide compounds according to formula (I) or formula (II) will typically be present in an amount sufficient to provide an emulsion which resists phase separation for at least two weeks at room temperature (~25° C.), and preferably for at least two weeks at 110° F. and/or at least two weeks at 40° F. In preferred embodiments, the emulsions will be stable at room temperature for at least four weeks, at least eight weeks, at least three months, at least six months, or even at least one year or more.

The glutamide compounds according to formula (I) or formula (II) will typically be present in an amount of from about 0.005% to about 3.0% by weight of the emulsion, but will more typically be present in an amount of from about 0.01% to about 0.8% by weight, or from about 0.015% to about 0.5% by weight, or from about 0.02% to about 0.1% by weight or from about 0.025% to about 0.06% by weight, or from about 0.03% to about 0.05% by weight of the emulsion.

The glutamide compounds according to formula (I) or formula (II) are typically crystalline solids at room temperature. It is not necessary to melt the glutamide compounds prior to addition to the compositions, nor is it necessary to prepare a premix of the glutamide compounds dissolved in a solvent. Moreover, it is not necessary to heat the composition containing the two phases in order to dissolve the glutamide compounds, and in some embodiments it is desirable to avoid heating the compositions, particularly where the silicone phase comprises volatile materials which pose a fire or explosion hazard if heated. It has surprisingly been found that the glutamide compounds can be dissolved in a composition comprising a silicone phase and a water phase by adding ethanol to the composition. Ethanol enables the glutamide compounds to be dissolved without first melting them, preparing a pre-mix, or heating the composition.

The emulsions according to the invention will preferably comprise an amount of ethanol sufficient to dissolve the glutamide compound in the composition containing the two phases at room temperature. Preferably, the glutamide will dissolve at a temperature less than 40° C., including temperatures between 20° C. and 30° C., and about 25° C.

Preferably, an amount of ethanol will be sufficient to improve the freeze-thaw stability of the emulsion. Typically, the emulsions will contain from about 0.1% to about 40% by weight ethanol, and more typically will comprise from about 1 to about 25% by weight ethanol. In various embodiments, the emulsions will contain from about 2.5 to about 17.5% by weight ethanol, from about 5 to about 15% by weight ethanol, or from about 7.5% to about 12.5% by weight ethanol.

The emulsions according to the invention may comprise an aqueous discontinuous phase and an oily continuous phase, a glutamide compound according to formulas (I) or (II), and an amount of ethanol sufficient to dissolve the glutamide compound in either of the two phases without heating the composition.

The oily continuous phase preferably contains a silicone oil, and more preferred is a volatile silicone oil. By volatile silicone is meant that the oil readily evaporates at ambient temperatures, e.g., about 25° C. Typically, volatile silicone oils will exhibit a vapor pressure ranging from about 1 Pa to about 2 kPa at 25° C.; will preferably have a viscosity of from about 0.1 to about 10 centistokes, preferably about 5 centistokes or less, more preferably about 2 centistokes or less, at 25° C.; and will boil at atmospheric pressure at from about 35° C. to about 250° C. Volatile silicones include cyclic and linear volatile dimethylsiloxane silicones, including 0.5 cst dimethicone, 0.65 cst dimethicone, 1 cst dimethicone, and 1.5 cst dimethicone. In one embodiment, the volatile silicones may include cyclodimethicones, including tetramer (D4), pentamer (D5), and hexamer (D6) cyclomethicones, or mixtures thereof. Suitable dimethicones are available from Dow Corning under the name Dow Corning 200® Fluid and have viscosities ranging from 0.65 to 5 centistokes. Suitable non-polar, volatile liquid silicone oils are disclosed in U.S. Pat. No. 4,781,917, herein incorporated by reference in its entirety. Additional volatile silicones materials are described in Todd et al., "Volatile Silicone Fluids for Cosmetics," Cosmetics and Toiletries, 91:27-32 (1976), herein incorporated by reference in its entirety. Linear volatile silicones generally have a viscosity of less than about 5 centistokes at 25° C., whereas the cyclic silicones have viscosities of less than about 10 centistokes at 25° C. Examples of volatile silicones of varying viscosities include Dow Corning 200, Dow Corning 244, Dow Corning 245, Dow Corning 344, and Dow Corning 345, (Dow Corning Corp.); SF-1204 and SF-1202 Silicone Fluids (Momentive Performance Materials), VS 7207 and 7158 (Momentive Performance Materials); and SWS-03314 (SWS Silicones Corp.). Linear, volatile silicones include low molecular weight polydimethylsiloxane compounds such as methyltrimethicone, trisiloxane, hexamethyldisiloxane, octamethyltrisiloxane, decamethyltetrasiloxane, and dodecamethylpentasiloxane to name a few.

Particularly preferred volatile silicones of the present invention include cyclomethicone tetramer, cyclomethicone pentamer, cyclomethicone hexamer, trisiloxane, methyl trimethicone or combinations thereof. Cyclomethicone pentamer is the currently preferred volatile silicone oil and in various embodiments, the cyclomethicone pentamer may constitute from about 5% to about 99% by weight of the oil phase, more typically from about 20% to about 98% by weight of the oil phase, and preferably, from about 40% to about 95% by weight of the oil phase.

The oil phase may include other volatile solvents. Typically, a volatile solvent may have a vapor pressure of above about 0.01 mmHg at 20° C. and evaporate at ambient temperatures. Volatile solvents may include volatile $C_{5-12}$ hydrocarbons (e.g., isododecane), aromatic hydrocarbons (e.g., xylenes, toluene, etc.), ketones (e.g., actetone, methylethyl ketone, etc.), ethers (e.g., diethyl ether, methylethyl ether, etc.), perfluorohydrocarbons, hydrofluoroethers, Freons, volatile silicones (e.g., cyclopentasiloxane), lower alcohols (e.g., isopropyl alcohol, etc.), esters of acetic acid (e.g., ethylacetate, butylacetate, etc.) and the like.

Among the volatile $C_{5-12}$ hydrocarbons, special mention may be made of isododecane which is available under the trade name Permethyl-99A (Presperse Inc.). Suitable fluorinated solvents include, without limitation, perfluoroethers, perfluorodecalin, perfluoromethyldecalin, perfluorohexane, perfluoromethylcyclohexane, perfluorodimethylcyclohexane, perfluoroheptane, perfluorooctane, perfluorononane, and perfluoromethylcycopentane, for example.

In a further embodiment, the compositions according to the invention will comprise ethanol, preferably anhydrous, in combination with one or more solvents having a vapor pressure at 25° C. which is less than the vapor pressure of ethanol. In another embodiment, the compositions according to the invention will comprise ethanol, preferably anhydrous, in combination with one or more solvents having a vapor pressure at 25° C. which is greater than the vapor pressure of ethanol.

In a preferred embodiment, the continuous phase will comprise cyclomethicone pentamer, and the discontinuous phase will comprise water and ethanol, the weight ratio of water to ethanol typically ranging from about 99:1 to about 1:99, more typically from about 25:1 to about 1:25, and preferably from about 9:1 to about 1:9, and more preferred still, from about 5:1 to about 1:1.

Preferably, the volatile silicone (e.g., cyclomethicone pentamer) will comprise from about 20% to about 90% of the emulsion, ethanol will comprise from about 1% to about 30% by weight of the emulsion, and water will comprise from about 5% to about 75% by weight of the emulsion, with the proviso that the total amount of volatile silicone, water, and ethanol does not exceed 100%. More particularly, the volatile silicone (e.g., cyclomethicone pentamer) will comprise from about 40% to about 70% of the emulsion, ethanol will comprise from about 5% to about 20% by weight of the emulsion, and water will comprise from about 20% to about 50% by weight of the emulsion.

The oil phase may comprise one or more volatile or non-volatile oils in addition to the silicone oil. Suitable non-limiting examples of oils for the continuous phase include natural and synthetic oils, including animal, vegetable, and petroleum oils; fatty acid triglycerides; fatty acid esters such as octyl palmitate, isopropyl myristate and isopropyl palmitate; ethers such as dicapryl ether; fatty alcohols such as cetyl alcohol, stearyl alcohol and behenyl alcohol; sterols; hydrocarbons such as isooctane, isododecane, isohexadecane, decane, dodecane, tetradecane, tridecane, $C_{8-20}$ isoparaffins, mineral oil, petrolatum, isoeicosane and polyisobutene; $C_{10-30}$ cholesterol/lanosterol esters; lanolin; and the like. Representative hydrocarbons include paraffinic hydrocarbons available from Exxon under the ISOPARS trademark, and from the Permethyl Corporation. In addition, $C_{8-20}$ paraffinic hydrocarbons such as $C_{12}$ isoparaffin (isododecane) manufactured by the Permethyl Corporation having the tradename Permethyl 99A™ are also contemplated to be suitable. Various commercially available $C_{16}$ isoparaffins, such as isohexadecane (having the tradename Permethyl R™) are also suitable. Silicone oils such as dimethicones, cyclic silicones, and polysiloxanes may also be included in the continuous phase. Non-volatile silicone oils will typically comprise polyalkylsiloxanes, polyarylsiloxanes, polyalkylarylsiloxanes, or mixtures thereof. Polydimethylsiloxanes are preferred non-volatile silicone oils. The non-volatile silicone oils will typically have a viscosity from about 10 to about 60,000 centistokes at 25° C., preferably between about 10 and about 10,000 centistokes, and more preferred still between about 10 and about 500 centistokes; and a boiling point greater than 250° C. at atmospheric pressure. Non-limiting examples include dimethyl polysiloxane(dimethicone), phenyl trimethicone, and diphenyldimethicone. The volatile and non-volatile silicone oils may optionally be substituted will various functional groups such as alkyl, aryl, amine groups, vinyl, hydroxyl, haloalkyl groups, alkylaryl groups, and acrylate groups, to name a few. In one embodiment, non-volatile oils, if present, will comprise less than about 5% by weight of the continuous phase.

The discontinuous phase will typically be composed of water, and ethanol. The discontinuous phase may further comprise one or more alcohols or polyhydric alcohols, such as without limitation methanol, isopropyl alcohol, or humectants such as the $C_{3-8}$ glycols, including glycerin, propylene glycol, butylene glycol, pentylene glycol, neopentyl glycol, or caprylyl glycol. The discontinuous phase may also comprise polyethylene glycols such as ethoxydiglycol.

The continuous phase will typically comprise from about 40% to about 95% of the emulsion, while the discontinuous phase will typically comprise from about 5% to about 60% of the emulsion. All ratios within the above limits are also contemplated. For example, the continuous phase may comprise about 45%, about 50%, about 55%, about 60%, about 65%, about 70%, about 75%, about 80%, about 85%, about 90%, or any other value within this range. Similarly, the discontinuous phase may comprise about 10%, about 15%, about 20%, about 25%, about 30%, about 35%, about 40%, about 45%, about 50%, about 55%, or any other value within this range.

The emulsions according to the invention may optionally further comprise one or more emulsifiers. For example, the one or more emulsifiers may be present in a total range from about 0.01% to about 10.0% by weight of the emulsion. In some embodiments, the total amount of emulsifier ranges from about 0.1% to about 6.0% be weight, or from about 0.5% to about 4.0% by weight. The amount of emulsifier will typically be from about 0.001 to about 10% by weight, but preferably will range from about 0.01 to about 5% by weight, more preferably from 0.1 to 3%, and most preferably about 0.25 to about 1% by weight, based upon the total weight of the composition. In other embodiments, the emulsifier may be absent.

The water-in-silicone emulsion is preferably emulsified with a nonionic surfactant (emulsifier). For water in oil emulsions, the emulsifier itself should be of low Hydrophilic-Lipophilic Balance (HLB), preferably below 10, more preferably below 8.5. While combinations of more than one emulsifier are contemplated to be within the scope of the invention, each such emulsifier, individually, should ideally be of low HLB. If present, the amount of emulsifier having an HLB above 10 will preferably be less than 1% by weight, more preferably less than 0.5% by weight, and more preferred still, less than 0.2% by weight.

Where the emulsifier is of the polyethoxylated type (e.g., polyoxyethylene ethers or esters) comprising chains of the form $-(CH_2CH_2O)_n-$, it is preferred that "n" be less than 20, more preferably less than 10, most preferably less than 5. Propoxylated emulsifiers e also contemplated to be suitable. Propoxylated emulsifiers also preferably having less than 20, more preferably less than 10, most preferably less than 5 propylene oxide repeat units.

Liquid or low melting temperature emulsifiers that can be used in the composition of the present invention include, but are not limited to, one or more of the following: sorbitan esters; polyglyceryl-3-diisostearate; sorbitan monostearate, sorbitan tristearate, sorbitan sesquioleate, sorbitan monooleate; glycerol esters such as glycerol monostearate and glycerol monooleate; polyoxyethylene phenols such as polyoxyethylene octyl phenol and polyoxyethylene nonyl phenol; polyoxyethylene ethers such as polyoxyethylene cetyl ether and polyoxyethylene stearyl ether; polyoxyethylene glycol esters; polyoxyethylene sorbitan esters; dimethicone copolyols; polyglyceryl esters such as polyglyceryl-3-diisostearate; glyceryl laurate; Steareth-2, Steareth-10, and Steareth-20, to name a few.

An example of a very low HLB emulsifier contemplated to be suitable according to the invention is Span 83, a sesquiester of monooleate and dioleate at a 2:1 molar ratio which has an HLB of 3.7. Sorbitan monostearate (INCI) is another suitable emulsifier, having an HLB value of 4.7. Additional emulsifiers are provided in the INCI Ingredient Dictionary and Handbook, $12^{th}$ Edition, 2008, the disclosure of which is hereby incorporated by reference.

Other suitable emulsifiers include polydiorganosiloxane-polyoxyalkylene block copolymers, including those described in U.S. Pat. No. 4,122,029, the disclosure of which is hereby incorporated by reference. These emulsifiers generally comprise a polydiorganosiloxane backbone, typically polydimethylsiloxane, having side chains comprising -$(EO)_m$- and/or -$(PO)_n$-groups, where EO is ethyleneoxy and PO is 1,2-propyleneoxy, the side chains typically being capped or terminated with hydrogen or lower alkyl groups (e.g., $C_{1-6}$, typically $C_{1-3}$). The side chains will preferably comprise 50 EU and/or PO units or less (e.g., m+n=<50), preferably 20 or less, and more preferably 10 or less. In addition to the alkoxylated side chain, the silicone emulsifier may also comprise alkyl chains pendant from the silicone backbone. Other suitable water-in-silicone emulsifiers are disclosed in U.S. Pat. No. 6,685,952, the disclosure of which is hereby incorporated by reference herein. Commercially available water-in-silicone emulsifiers include those available from Dow Corning under the trade designations 3225C and 5225C FORMULATION AID; SILICONE SF-1528 available from Momentive Performance Materials; ABIL EM 90 and EM 97, available from Goldschmidt Chemical Corporation (Hopewell, Va.); and the SILWET™ series of emulsifiers sold by OSI Specialties (Danbury, Conn.).

Examples of water-in-silicone emulsifiers include, without limitation, PEG/PPG-18/18 dimethicone (trade name 5225C, Dow Corning), PEG/PPG-19/19 dimethicone (trade name BY25-337, Dow Corning), Cetyl PEG/PPG-10/1 dimethicone (trade name Abil EM-90, Goldschmidt Chemical Corporation), PEG-12 dimethicone (trade name SF 1288, Momentive Performance Materials), lauryl PEG/PPG-18/18 methicone (trade name 5200 FORMULATION AID, Dow Corning), PEG-12 dimethicone crosspolymer (trade name 9010 and 9011 silicone elastomer blend, Dow Corning), PEG-10 dimethicone crosspolymer (trade name KSG-20, Shin-Etsu), and dimethicone PEG-10/15 crosspolymer (trade name KSG-210, Shin-Etsu).

The preferred emulsifiers will comprise an organosiloxane polymer having side chains comprising -$(EO)_m$- and/or -$(PO)_n$-groups, where the sum of n and m is about 50 or less, the side chains being terminated with hydrogen or $C_{1-8}$ alkyl groups, such as, for example, PEG10-dimethicone.

The compositions of the invention may comprise one or more film formers, preferably a hydrophobic film-former. The hydrophobic film former may be any hydrophobic material suitable for use in a cosmetic composition including, waxes and oils, but is preferably a hydrophobic film-forming polymer. The term film-forming polymer may be understood to indicate a polymer which is capable, by itself or in the presence of at least one auxiliary film-forming agent, of forming a continuous film which adheres to a surface and functions as a binder for the particulate material. The term "hydrophobic" film-forming polymer will typically refer to a polymer with a solubility in water at 25° C. of less than about 1% by weight or one in which the monomeric units of the polymer individually have a solubility in water of less than about 1% by weight at 25° C. A "hydrophobic" film forming polymer will partition predominately into the octanol phase when shaken with a mixture of equal volumes of water and octanol. By predominately is meant more the 50% by weight, but preferably more than 75% by weight, more preferably more than 95% by weight will partition into the octanol phase.

Polymeric film formers include polyolefins, polyvinyls, polacrylates, polyurethanes, silicones, silicone acrylates, polyamides, polyesters, fluoropolymers, polyethers, polyacetates, polycarbonates, polyimides, rubbers, epoxys, formaldehyde resins, and homopolymers and copolymers of any of the foregoing. The film former is preferably silicone based. By "silicone based" is meant that the hydrophobic film former comprises at least one silicone moiety, such as, for example, dimethicone, amodimethicone, dimethiconol, silicone polyurethane, silicone acrylate or combinations thereof. Particular mention may be made of the silicone acrylate copolymers, in particular copolymers comprising a poly (alkyl)acrylate backbone and a dimethicone polymer grafted to an alkyl ester side chain, such as the commercially available film former Cyclopentasiloxane (and) Acrylates/Dimethicone Copolymer (KP-545, Shin-Etsu Chemical Co., Ltd) and Methyl Trimethicone (and) Acrylates/dimethicone Copolymer (KP-549, Shin-Etsu Chemical Co., Ltd.)

Other preferred polymeric film formers include dimethicone, dimethiconol, acrylates, alkyl acrylates, polyurethanes), Amino Bispropyl Dimethicone, Aminopropyl Dimethicone, Amodimethicone, Amodimethicone Hydroxystearate, Behenoxy Dimethicone, $C_{30-45}$ Alkyl Dimethicone, $C_{24-28}$ Alkyl Dimethicone, $C_{30-45}$ Alkyl Methicone, Cetearyl Methicone, Cetyl Dimethicone, Dimethicone, Dimethoxysilyl Ethylenediaminopropyl Dimethicone, Hexyl Methicone, Hydroxypropyldimethicone, Stearamidopropyl Dimethicone, Stearoxy Dimethicone, Stearyl Methicone, Stearyl Dimethicone and Vinyl Dimethicone. Particularly preferred are silicone polymers, including Methicone (as described by CTFA Monograph No. 1581, which is incorporated herein by reference), Dimethicones (as described by CTFA Monograph No. 840, which is incorporated herein by reference) and Amodimethicones as described by CTFA Monograph No. 189, which is incorporated herein by reference). All CTFA Monographs provided herein are found in the International Cosmetic Ingredient Dictionary and Handbook, 12$^{th}$ Edition (2008), and are hereby incorporated by reference.

In one embodiment of the invention, the compositions include a silicone gum. Suitable silicone gums will typically have a molecular weight of from about 200,000 to about 600,000. Specific examples include polydimethylsiloxane, (polydimethylsiloxane)(methylvinylsiloxane)copolymer, poly(dimethylsiloxane)(diphenyl)(methylvinylsiloxane)copolymer, dimethiconol, fluorosilicone, dimethicone, or mixtures thereof. In a preferred embodiment, the film forming silicone gum is a high molecular weight Dimethicone. The high molecular weight Dimethicones have high viscosities and are commonly referred to as dimethicone gums. The viscosity of the silicone gum may be, without limitation, form about 500,000 centistokes to about 100 million centistokes measured at 25° C. The high molecular weight Dimethicones are commercially available in combination with lower molecular weight silicones or with volatile silicones, which makes the high molecular weight Dimethicones easier to handle. A suitable mixture containing high molecular weight Dimethicone (MW approx 500,000) is commercially available from Momentive under the trade name SF 1214.

In another preferred embodiment, the film forming polymer is a silicone acrylate, such as that having the CTFA Monograph No. 10082 and the INCI name Acylates/Dimethicone. This polymer is commercially available from Shin-Etsu Chemical Co., Ltd. under the trade name KP-544 and comprises grafted copolymers with an acrylic polymer backbone and dimethylpolysiloxane side chains. The same polymer is commercially available in a variety of different solvents including Isopropyl Alcohol (KP-541), Butyl Acetate (KP-543), Cyclopentasiloxane (KP-545), Methyl Trimethicone (KP-549), and Isododecane (KP-550), each of which is contemplated to be useful.

In another embodiment, the film forming polymer may be a silicone urethane, such as that having the INCI Name Bis-Hydroxypropyl Dimethicone/SMDI Copolymer and the INCI Monograph ID No. 22006. This polymer is commercially available from Siltech Corp. under the trade name SILMER UR-5050, which comprises the polymer in Isododecane.

Other film formers that may be employed include, without limitation, natural, mineral and/or synthetic waxes. Natural waxes are those of animal origin, including without limitation beeswax, spermaceti, lanolin, and shellac wax, and those of vegetable origin, including without limitation carnauba, candelilla, bayberry, and sugarcane wax, and the like. Mineral waxes contemplated to be useful include, without limitation ozokerite, ceresin, montan, paraffin, microcrystalline, petroleum, and petrolatum waxes. Synthetic waxes include, for example, Fischer Tropsch (FT) waxes and polyolefin waxes, such as ethylene homopolymers, ethylene-propylene copolymers, and ethylene-hexene copolymers. Representative ethylene homopolymer waxes are commercially available under the tradename POLYWAX® Polyethylene (Baker Hughes Incorporated). Commercially available ethylene-α-olefin copolymer waxes include those sold under the tradename PETROLITE® Copolymers (Baker Hughes Incorporated). Another wax that is suitable is dimethiconol beeswax available from Noveon as ULTRABEE™ dimethiconol ester.

High molecular weight hydrophobic esters may also be useful. The hydrophobic ester may be saturated or unsaturated and may include without limitation, mono-esters of fatty acids, diesters of diacids, diesters of triacids, and triesters of triacids. Monoesters include the esterification products of straight chained, branched, or cyclic $C_4$-$C_{24}$, preferably $C_8$-$C_{24}$, and more preferably $C_{12}$-$C_{22}$ monocarboxylic acids with straight chained, branched, or cyclic $C_4$-$C_{36}$, preferably $C_8$-$C_{24}$, and more preferably $C_{12}$-$C_{18}$ alcohols. Diesters include the esterification products of straight chained, branched, or cyclic $C_4$-$C_{48}$ dicarboxylic acids, typically $C_8$-$C_{44}$ dicarboxylic acids, and more typically $C_{12}$-$C_{36}$ dicarboxylic acids, with straight chained, branched, or cyclic $C_4$-$C_{36}$, preferably $C_8$-$C_{24}$, and more preferably $C_{12}$-$C_{28}$ alcohols. The dicarboxylic acid may be, for example, a dimer acid formed by the dimerization of an unsaturated fatty alcohol, e.g., linoleic acid. Diesters and triesters of triacids include the esterification products of $C_6$-$C_{72}$ tricarboxylic acids, typically $C_{12}$-$C_{66}$ tricarboxylic acids, with $C_4$-$C_{36}$, preferably $C_8$-$C_{24}$, and more preferably $C_{12}$-$C_{18}$ alcohols. The tricarboxylic acid may be, for example, a trimer acid formed by the trimerization of an unsaturated fatty alcohol, e.g., linoleic acid. The esters are preferably high molecular weight esters by which is meant that the molecular weight is at least 500. In some embodiments, the molecular weight of the ester will be at least 750, at least 1000, or at least 1200. The esters are preferably hydrophobic and may optionally be dispersible but not soluble in the vehicle. One suitable hydrophobic ester is Triisostearyl Trilinoleate (INCI) (CAS Registry No. 103213-22-5), which is available from Lubrizol Advanced Materials, Inc. under the trade name SCHERCEMOL™ TIST Ester.

In some embodiments, it may be desirable to add some amount of a hydrophilic or water-soluble film former (e.g., cellulosics, polysaccharides, polyquaterniums (such as polyquaternium-37 (INCI), etc.) to the composition to improve spreading, emulsion stability, aesthetic look and feel, etc. In some embodiments, the collective weight percentage of hydrophilic or water-soluble film formers will be from about 0.001% by weight to less than about 20%, preferably less than about 15%, more preferably less than about 10%, and more preferred still, less than about 5% by weight based on the total weight of the composition. In one embodiment, hydrophilic film formers will comprise less than about 2.5% by weight of the total weight of the composition. In other embodiments, the composition is substantially free of water-soluble film formers by which is meant that the composition comprise less than 2% by weight, preferably, less than 1% by weight, and more preferred still, less than 0.5% by weight, or less than 0.1% by weight of such water-soluble film-formers. In one embodiment the composition does not contain a hydrophilic film former.

Combinations of any of the foregoing film formers are also contemplated to be suitable, including combinations or polymeric and non-polymeric film formers.

The film formers will comprise from about 0.01% to about 20% by weight of the composition, and more typically will comprise from about 0.25% to about 15%, and preferably from about 1 to 12%, more preferably from 1.5% to about 10%, and more preferred still about 3% to about 8% by weight of the composition.

In certain embodiments, the composition will comprise a silicone acrylate film former and a silicone gum film former. The silicone acrylate film former and the silicone gum film former may each independently comprise from about 0.01% to about 20% by weight of the composition, and more typically will comprise from about 0.25% to about 15%, and preferably from about 1.0% to about 10%, and more preferably, from 1.5% to about 8%, and more preferred still about 3% to about 5% by weight of the composition.

The compositions of the invention may also comprise particular materials which may be inorganic or organic, hydrophobic or hydrophilic. The preferred compositions will comprise one or more particulate materials which are either hydrophobic by nature or have been hydrophobically modified by surface treatment or the like.

In one embodiment, the particulate material may comprise at least one hydrophobic particulate material which has a coefficient of dynamic (kinematic) friction, $\mu_k$, greater than 0.5. The particulate material may have spherical or substantially non-spherical shapes. The high drag of the high $\mu_k$ particles may increase the substantivity of the particles against a human integument.

A preferred particulate material according to the invention is hydrophobically modified aluminum oxide ($Al_2O_3$), also known as alumina, particularly fumed (or pyrogenic) alumina. Hydrophobically modified silica ($SiO_2$), including fumed silica, may have a particle size range from about 7 nm to about 40 nm and an aggregate particle size between about 100 and about 400 nm, and is also contemplated to be particularly useful. Other notable particulate materials are hydrophobically modified metal oxides, including without limitation titanium dioxide ($TiO_2$), iron oxides (FeO, $Fe_2O_3$ or $Fe_3O_4$), zirconium dioxide ($ZrO_2$), tin dioxide ($SnO_2$), zinc oxide (ZnO), and combinations thereof.

Advantageously, the particulate material may be one which provides additional functionality to the compositions, including for example, ultraviolet (UV) light absorption or scattering, in the case of, for example, titanium dioxide and zinc oxide particulates, or provide aesthetic characteristics, such as color (e.g., pigments), pearlesence (e.g. mica), or the like. The particulate material may be based, for example, on organic or inorganic particulate pigments. Examples of organic particulate pigments include lakes, especially aluminum lakes, strontium lakes, barium lakes, and the like. Examples of the inorganic particulate pigments are silica, alumina, carbon black, iron oxide, especially red, yellow and black iron oxides, titanium dioxide, zinc oxide, potassium ferricyanide ($K_3Fe(CN)_6$), potassium ferrocyanide ($K_4Fe(CN)_6$), potassium ferrocyanide trihydrate ($K_4Fe(CN)_6.3H_2O$), and mixtures thereof. The particulate material may also be based on inorganic fillers such as talc, mica, silica, and mixtures thereof, or any of the clays disclosed in EP 1 640 419, the disclosure of which is hereby incorporated by reference.

In one embodiment, particulate materials are surface-treated to impart a hydrophobic coating thereon. As used herein, a hydrophobically-modified particle is one which is rendered less hydrophilic or more hydrophobic by surface modification as compared to the particle in the absence of surface modification. In one embodiment, a hydrophobic particle in accordance with an embodiment of the present invention may be formed from an oxide particle (e.g., a metal oxide, silicon dioxide, etc.) having its surface covered with (e.g., covalently bonded to) non-polar radicals, such as for example alkyl groups, silicones, siloxanes, alkylsiloxanes, organosiloxanes, fluorinated siloxanes, perfluorosiloxanes, organosilanes, alkylsilanes, fluorinated silanes, perfluorinated silanes and/or disilazanes and the like. The surface treatment may be any such treatment that makes the particles more hydrophobic. A preferred hydrophobic coating according to the invention is prepared by treating an oxide, for example, alumina, with Trimethoxycaprylyl Silane.

Any of the hydrophobically modified particulate materials described in U.S. Pat. No. 6,683,126 to Keller et al., the disclosure of which is hereby incorporated by reference herein, are also contemplated to be useful, including without limitation those obtained by treating an oxide material (e.g., $SiO_2$, $TiO_2$, etc.) with a (perfluoro)alkyl-containing compound that contains at least one reactive functional group that undergoes a chemical reaction with the near-surface OH groups of the oxide support particle, including for example hexamethyldisilazane, octyltrimethoxysilane, silicone oil, chlorotrimethylsilane, and dichlorodimethylsilane.

In one particular preferred embodiment, the particulate material is a fumed (or pyrogenic) alumina and/or a fumed (or pyrogenic) silica which is surface-functionalized with alkylsilyl, fluoro-alkylsilyl, or perfluoro-alkylsilyl groups, preferably with alkylsilyl groups (i.e., surface treated with alkylsilanes). Typically, the alkylsilyl groups will comprise $C_{1-20}$ hydrocarbons (more typically $C_{1-8}$ hydrocarbons) which are optionally fluorinated or perfluorinated. Such groups may be introduced by reacting at the particle surface with silanes such as $C_{1-12}$-alkyl-trialkoxysilanes (e.g., $C_{1-12}$-alkyl-trimethoxysilanes or $C_{1-12}$-alkyl-triethoxysilanes). Preferably, the particle surface is functionalized with alkylsilyl groups which may be accomplished by treating the surface with alkylsilanes. More preferably, the particle surface is functionalized and surface modified with octylsilyl groups, also known as caprylylsilyl groups, introduced by reacting the particles with, octylsilanes (or caprylylsilanes), for example, trimethoxycaprylylsilane or triethoxycaprylylsilane. Such particles are commonly referred to as octylsilane treated. Because the particles are preferably fumed, the primary particle size will typically be very small, on the order of 5 nm to about 30 nm. The specific surface area (SSA) of these particulate materials will typically, but not necessarily, range from about 50 to about 300 $m^2/g$, more typically, from about 75 to about 250 $m^2/g$, and preferably from about 100 to about 200 $m^2/g$.

A suitable hydrophobically-modified alumina particulate includes fumed aluminum oxide treated with octylsilane (obtained by reacting trimethoxyoctylsilane with fumed alumina), such as AEROXIDE™ ALU C805 from Evonik Industries. That product is believed to have an average primary particle size of about 13 nm (nanometers) and a specific surface area (SSA) of about 100±15 $m^2/g$. Typically, the alumina or hydrophobically-modified alumina has not been calcined, by which is meant that the alumina has not been heated to a high temperature, for example, at a temperature above 1000° C. to expel volatile impurities in the crude metal oxide. Preferably, the particulate material is substantially free of calcined alumina, by which is meant that calcined alumina is not deliberately added to the particulate material and the amounts are so low as to not have a measureable impact on the performance, look or feel of the composition. More preferably, the particulate material is free of calcined alumina.

In other embodiments, the compositions may be substantially free of alumina or hydrophobically-modified alumina. By substantially free of alumina or hydrophobically-modified alumina means that these components comprise less than about 2%, preferably less than about 1%, and more preferably less than about 0.5% by weight of the one or more particulate materials.

Additional particles may he included, such as hydrophobically-modified fumed silica. When present, suitable hydrophobically-modified fumed silica particles include, but are not limited to AEROSIL™ R 202, AEROSIL™ R 805, AEROSIL™ R 812, AEROSIL™ R 812 S, AEROSIL™ R 972; AEROSIL™ R 974, AEROSIL™ R 8200, AEROX- IDE™ LE-1, AEROXIDE™ LE-2, and AEROXIDE™ LE-3 from Evonik/Degussa Corporation of Parsippany, N.J., which are believed to be hydrophobic fumed silicas, surface-functionalized with alkylsilyl groups for hydrophobicity and a specific surface area (SSA) between about 100±30 m$^2$/g and about 220±30 m$^2$/g. The hydrophobically-modified silica materials described in U.S. Patent Pub. 2006/0110542 to Dietz et al., incorporated herein by reference, are also contemplated to be particularly suitable.

While silica (SiO$_2$) and hydrophobically-modified silicas are contemplated to be useful in some embodiments, in other embodiments the compositions will be substantially free of silica or hydrophobically-modified silica. By substantially free of silica or hydrophobically-modified silica means that these components comprise less than about 2%, preferably less than about 1%, and more preferably less than about 0.5% by weight of the one or more particulate materials. In other embodiments the compositions will be free of silica or hydrophobically modified silica. By "free" of is meant that none is deliberately added and any amounts present will be so low as to not impact the look, feel or performance of the composition.

The one or more particulate materials may also comprise particulate organic polymers such as polytetrafluoroethylene, polyethylene, polypropylene, nylon, polyvinyl chloride, and the like which have been formed into fine powders. Alternatively, the particulate material may be a microcapsule comprising any of the shell materials described in U.S. Patent Pub. 2005/0000531, the disclosure of which is hereby incorporated by reference herein. Other optional particulates include the particulate silicone wax sold under the trade name Tegotop™ 105 (Degussa/Goldschmidt Chemical Corporation) and the particulate vinyl polymer sold under the name Mincor™ 300 (BASF).

The one or more particulate materials will typically be in the form of a powder having a median particle size between about 1 nm (nanometers) and about 1 mm (millimeters), more typically between about 5 nm and about 500 µm (micrometer), preferably between about 7 nm and about 100 µm, more preferably between about 10 nm and about 5 µm about 20 µm, about 50 µm, or about 75 µm. Where more than one particulate material is employed (e.g., modified TiO$_2$ and modified SiO$_2$), the median particle size of each powder is preferably within the foregoing ranges.

Typically, the one or more hydrophobic or hydrophobically modified particulate materials, especially the alumina and/or silica maprticulates, with or without an octylsilane surface treatment, will typically comprise from about 0.01% to about 10% by weight of the total composition, more typically from about 0.1% to about 5%, preferably from about 0.1% to about 2.5%, more preferably from about 0.25% to about 2.0% by weight of the composition, and most preferably from about 0.4% to about 1.5%. In certain embodiments, the one or more particulate material may comprise about 0.4%, about 0.5%, about 0.6%, about 0.7%, about 0.8%, about 0.9%, about 1.0%, about 1.25% and about 1.5% by weight of the composition.

Generally, the weight ratio of the one or more hydrophobic particulate materials to the one or more film formers will be from about 1:1 to about 1:100, about 1:1.25 to about 1:75, about 1:1.5 to about 1:50, about 1:1.75 to about 1:25, or about 1:2 to about 1:10. In various implementations, the ratio of one or more hydrophobic particulate materials to one or more film formers will be about 1:20, about 1:15, about 1:10, about 1:9, about 1:8, about 1:7, about 1:6, about 1:5, about 1:4, about 1:3, about 1:2, about 1:1.5, or about 1:1.

In one embodiment of the invention, the one or more hydrophobic particulate material and the film former are first dispersed or dissolved in the oil or silicone phase of a water-in-oil or water-in-silicone emulsion. The or silicone is subsequently mixed with the aqueous phase to form the emulsion. The emulsions will typically have the hydrophobic film formers and any hydrophobic pigments dispersed or dissolved predominantly in the oil or silicone phase.

Emulsions according to the invention are particularly suitable for cosmetic compositions for topical application. When formulated as cosmetic compositions, the emulsions will typically include additional components optionally distributed in either or both phases of the emulsion. Such components may be selected from the group consisting of pigments, waxes, emollients, humectants, thickeners, gellants, moisturizers, preservatives, flavorants, fragrances, antioxidants, botanicals, and mixtures thereof.

For example, the emulsions may comprise a shine-enhancing agent, in the case where the product is intended for application to hair. Shine agents include, without limitation, lens-shaped particles such as hemi-spherical PMMA, including the commercially available hemi-spherical methyl methacrylate crosspolymer sold under the trade name 3D Tech PW (Plain) XP (Kobo). Other suitable shine enhancers include phenylpropyldimethylsiloxysilicate, polybutene, polyisobutene, and hydrogenated polyisobutene. Silicone fluids, such as aryl-substituted siloxanes having high refractive indices are also useful as shine enhancers. Particular mention may be made of Phenyltrimethicone, which is available under the trade names SCI-TEC P™ 100 (ISP) and PDM20 (Wacker-Belsil), and Trimethylsiloxyphenyl Dimethicone (INCI name), which is available under the trade name PDM 1000 (Wacker-Belsil). The PDM20 material has a refractive index of 1.437 at 25° C. The PDM 1000 material has a refractory index of 1.461 at 25° C. Another suitable silicone fluid is trimethylsiloxyphenyl dimethicone. In general, any aryl-substituted silicone having a refractive index of greater than 1.4 at 25° C. is contemplated to be suitable for restoring shine to hair treated with the inventive compositions. Phenyl silicones such as pentaphenyl trimethyl trisiloxane or tetraphenyl tetramethyl trisiloxane, commercially available as HRl fluids from Dow corning HRI, are also useful for enhancing shine. Certain organic compounds, such as octyl methoxy cinnamate, may also be used to enhance shine.

The shine enhancer, if present, will typically comprise from about 0.01% to about 5% by weight of the total composition. More typically, the shine enhancer component will comprise from about 0.05% to about 2.5% by weight of the composition. Preferably, the shine enhancer will comprise from about 0.1% to about 1.5% by weight of the composition.

A third component according to some embodiments of the inventive compositions is a fluorosilicone, which can impart excellent spreading properties. The fluorosilicone is preferably hydrophobic and oleophobic and is also preferably insoluble but dispersible in the vehicle. There is essentially no restriction on the nature of the fluorosilicone. In one embodiment, the fluorosilicone will comprise a fluoro-substituted polyorganosiloxane. The fluorosilicone will typically comprise repeat units of the form —[Si(R$_2$)(R$_3$)—O]— wherein R$_2$ and/or R$_3$ are independently alkyl, aryl, or alkylaryl (e.g., benzyl) radicals, with at least one of R$_2$ and R$_3$ being substituted with one or more fluorine atoms. Preferably, at least one of R, or R$_3$ will be a C$_{1-30}$ alkyl group which comprises one or more fluorine atoms, and which preferably comprises a perfluoro segment, by which is meant a segment of the form —(CF$_2$)$_x$— where x is an integer from 1 to 29 and/or a trifluoromethyl group. One suitable fluorosilicone is Perfluorononyl Dimethicone sold under the trade names PECOSIL® FSL-150, FSL-300, FSH-150, FSH-300, FSU-150 and FSU-300 from Phoenix Chemical, Inc. which all have the chemical abstracts number CAS 259725-95-6.

In addition to the foregoing, the compositions according to the invention may comprise additional pigments, pearlescents, and/or colorants. Inorganic pigments include without limitation titanium dioxide, zinc oxide, iron oxides, chromium oxide, ferric blue, mica, bismuth oxychloride, and titinated mica; organic pigments include barium, strontium, calcium or aluminium lakes, ultramarines, and carbon black; colorants include without limitation D&C Green #3, D&C Yellow #5, and D&C Blue #1. Pigments and/or colorants may be coated or surface treated with one or more compatibilizers to aid in dispersion in the solvent. Preferred pigments and/or colorants are those surface treated to render them hydrophobic.

Preferred colorants include Iron Oxides, Black Oxide of Iron, Brown Iron Oxide, CI 77489, CI 77491, CI 77492, CI 77499, Iron Oxide Red 10-34-PC-2045, Pigment Black 11, Pigment Brown 6, Pigment Brown 7, Pigment Red 101, Pigment Red 102, Pigment Yellow 42, Pigment Yellow 43, Red Iron Oxide, Synthetic Iron Oxide, and Yellow Iron Oxide.

Various fillers and additional components may be added. Suitable fillers include without limitation silica, treated silica, talc, zinc stearate, mica, kaolin, Nylon powders such as Orgasol™, polyethylene powder, Teflon™, boron nitride, copolymer microspheres such as Expancel™ (Nobel Industries), Polytrap™ (Dow Corning) and silicone resin microbeads (Tospearl™ from Toshiba), and the like.

Additional pigment/powder fillers include, but are not limited to, inorganic powders such as gums, chalk, Fuller's earth, kaolin, sericite, muscovite, phlogopite, synthetic mica, lepidolite, biotite, lithia mica, vermiculite, aluminum silicate, starch, smectite clays, alkyl and/or trialkyl aryl ammonium smectites, chemically modified magnesium aluminum silicate, organically modified montmorillonite clay, hydrated aluminum silicate, aluminum starch octenyl succinate barium silicate, calcium silicate, magnesium silicate, strontium silicate, metal tungstate, magnesium, silica alumina, zeolite, barium sulfate, calcined calcium sulfate (calcined gypsum), calcium phosphate, fluorine apatite, hydroxyapatite, ceramic powder, metallic soap (zinc stearate, magnesium stearate, zinc myristate, calcium palmitate, and aluminum stearate), colloidal silicon dioxide, and boron nitride; organic powder such as polyamide resin powder (nylon powder), cyclodextrin, polymethylmethacrylate powder (PMMA), copolymer powder of styrene and acrylic acid, benzoguanamine resin powder, poly(ethylene tetrafluoride) powder, and carboxyvinyl polymer, cellulose powder such as hydroxyethyl cellulose and sodium carboxymethyl cellulose, ethylene glycol monostearate; inorganic white pigments such as magnesium oxide; and stabilizers/rheology modifiers, for example, Bentone Gel and Rheopearl TT2. Other useful powders are disclosed in U.S. Pat. No. 5,688,831, the disclosure of which is hereby incorporated by reference.

The aggregate amount of all such additional pigments, colorants, and fillers is not particularly restricted. Typically, all additional pigments, colorants, fillers, etc., if present, will collectively comprise from about 0.1% to about 5% of the total composition, but more typically will comprise from about 0.1% to about 2% by weight of the composition.

The compositions of the invention may optionally comprise other active and inactive ingredients typically associated with the intended cosmetic or personal care products. Suitable other ingredients include, but are not limited to, amino acids, antioxidants, conditioners, chelating agents, colorants, emollients, emulsifiers, excipients, fillers, fragrances, gelling agents, humectants, minerals, moisturizers, photostabilizing agents (e.g., UV absorbers), sunscreens, preservatives, stabilizers, staining agents, surfactants, viscosity and/or rheology modifiers, vitamins, waxes and mixtures thereof. The compositions may also include anti-dandruff and/or sunscreen ingredients. Collectively, all such additional components will typically comprise less than 5% by weight of the composition.

The emulsion and other multi-phase fluids may be formulated as skin care products, hair care products or the like. In a preferred embodiment, the emulsions are formulated as hair care products and may include additional components customarily found in such products, including shine agents and conditioners. Conditioners include polyquaterniums, such as polyquaternium-37.

EXAMPLES

A water-in-silicone emulsion stabilized with dibutyl ethylhexanoyl glutamide is provided in Table 1. The product is formulated as a leave-in hair product for reducing frizz and improving color retention in artificially colored hair.

TABLE 1

| INCI name/description | % |
|---|---|
| Alumina/Polycaprylylsilsesquioxane | 0.5 |
| Dimethicone gum | 4.8 |
| PEG-150/Decyl Alcohol/SMDI Copolymer | 0.18 |
| Acrylates/Dimethicone Copolymer/Methyl Trimethicone | 1.0 |
| Anti-foaming Agent | 0.25 |
| Sunscreens | 0.5 |
| Viscosity Increasing Agents | 1.5 |
| Hair conditioning agents | 3.9 |
| Preservatives | 0.8 |
| Fragrances | 0.8 |
| Dibutyl Ethylhexanoyl Glutamide | 0.01-0.5 |
| Anhydrous Alcohol | 10.0 |
| Demineralized Water | 26.5 |
| Cyclopentasiloxane | q.s. |
| Total: | 100.00 |

The water-in-silicone emulsion is stable at 77° F. and 110° F. for at least two weeks and is also stable over repeated freeze-thaw cycles between 40° F. and 110° F. The emulsion is made at room temperature.

The invention described and claimed herein is not to be limited in scope by the specific embodiments herein disclosed since these embodiments are intended as illustrations of several aspects of the invention. Any equivalent embodiments are intended to be within the scope of this invention. Indeed, various modifications of the invention in addition to those shown and described therein will become apparent to those skilled in the art from the foregoing description. Such modifications are also intended to fall within the scope of the appended claims. All publications cited herein are incorporated by reference in their entirety.

The invention claimed is:

1. A stabilized water-in-silicone emulsion comprising an oil phase, an aqueous phase, and a glutamide compound present in an amount of from about 0.02% to about 0.5% by weight of the emulsion, said glutamide compound consisting essentially of dibutyl ethylhexanoyl glutamide.

* * * * *